United States Patent [19]

Johansson et al.

[11] Patent Number: 5,100,916
[45] Date of Patent: Mar. 31, 1992

[54] CARBAMIC ACID ESTER FOR TREATMENT OF ADDICTION TO ALCOHOL

[75] Inventors: Benny Johansson, Malmö, Sweden; Erling Petersen, Glostrup; Elisabeth Arnold, Frederiksberg, both of Denmark

[73] Assignee: Bio-Tox Diagnostics Kommanditbolag, Sweden

[21] Appl. No.: 603,687

[22] PCT Filed: Mar. 29, 1989

[86] PCT No.: PCT/SE89/00161
§ 371 Date: Oct. 30, 1990
§ 102(e) Date: Oct. 30, 1990

[87] PCT Pub. No.: WO89/09208
PCT Pub. Date: Oct. 5, 1989

[30] Foreign Application Priority Data

Mar. 30, 1988 [DK] Denmark .............................. 1819/88

[51] Int. Cl.$^5$ ............................................ A61K 31/27
[52] U.S. Cl. ................................................... 514/478
[58] Field of Search ......................................... 514/478

[56] References Cited

U.S. PATENT DOCUMENTS

2,913,327 11/1959 Tilles et al. ............................ 71/2.7
4,678,809 7/1987 Phillips ................................ 514/599

FOREIGN PATENT DOCUMENTS

0169618 1/1986 European Pat. Off. .
2050439 4/1972 Fed. Rep. of Germany .
2625823 12/1976 Fed. Rep. of Germany .
51-138660 11/1976 Japan .
53-12424 2/1978 Japan .
868111 5/1961 United Kingdom .

OTHER PUBLICATIONS

Yourick & Faiman, 1987 *Biosis* #85042991 Diethyldithiocarbamic Acid Methyl Ester a Metabolite of Disulfiram and Its Alcohol Sensitizing Properties in the Disulfiram-Ethanol Reaction.
Mackerell et al., 1985, *Brosis* #28103228 Human Mitochondrial Aldehyde Dehydrogenase EC-1.2.1.3 Inhibition by Diethyldithiocarbamic Acid Methanethiol Mixed Disulfe a Derivative of Disulfiram.
Faiman et al., 1983, *Biosis* #77048045 Diethyldithiocarbamic Acid Methyl Ester Distribution Elimination and LD-50 in the Rat after Intraperitoneal Administration.
Pedersen, 1980, Biosis #71006066 Analysis and Preliminary Pharmacokinetics of Disulfiram.
H. Tilles, *J. Amer. Chem. Soc.*, 81, 714 (1959).

The Merck Index, 10th Ed., p. 1411, #9681.
Chemical Abstracts, 78, 1973, Abs. No. 106765d.
Chemical Abstracts, 79, 1973, Abs. No. 133487s.
Chemical Abstracts, 89, 1978, Abs. No. 158400c.
B. Johansson, *Pharmacology & Toxicology*, 64, 471–474 (1989).
B. Johansson et al., *Eur. J. Clin. Pharmacol.*, 37, 133–138 (1989).
T. Gessner et al., *Biochemical Pharmacology*, 21, 219–230 (1972).
R. A. Deitrich et al., *Molecular Pharmacology*, 7, 301–307 (1971).
K. J. Freundt et al., *Int. Arch. Occup. Environ. Hlth.*, 37, 35–46 (1976).
T. M. Kitson, *Biochem. J.*, 175, 83–90 (1978).
R. C. Vallari et al., *Science*, 216, 637–639 (1982).
R. A. Dietrich et al., *J. Biol. Chem.*, 238, 1683–1689 (1963).
T. M. Kitson et al., *Biochem. J.*, 155, 445–448 (1976).
A. H. Blair et al., *Can. J. of Biochem.*, 47, 265–272 (1968).
J. H. Stromme, *Biochim. Pharm.*, 12, 937–948 (1963).

*Primary Examiner*—Stanley J. Friedman
*Attorney, Agent, or Firm*—Merchant, Gould, Smith, Edell, Welter & Schmidt

[57] ABSTRACT

A preparation for treatment of addiction to alcohol, containing a carbamic acid ester having the general formula I

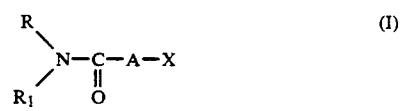

wherein X is —CH$_3$ or —CH$_2$CH$_3$, R and R$_1$ which may be the same or different, are hydrogen, C$_{1-5}$ alkyl or a group of the formula

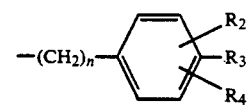

wherein n is 0, 1 or 2, and R$_2$, R$_3$ and R$_4$ are H, OH, OCH$_3$, CH$_3$, NO$_2$ or halogen, and wherein R and R$_1$ together with the nitrogen atom can form a saturated ring system having 4–6 atoms selected among C, N, O or S, and wherein A is sulphur or oxygen.

5 Claims, No Drawings

CARBAMIC ACID ESTER FOR TREATMENT OF ADDICTION TO ALCOHOL

The present invention relates to a carbamic acid ester for use as a drug. The invention also relates to a preparation for treatment of addiction to alcohol, and to the use of the carbamic acid ester for producing a preparation for treatment of addiction to alcohol.

Disulfiram (Antabuse ®) is widely used as a drug for treatment of addiction to alcohol. If a person takes disulfiram and then drinks alcohol, he experiences the unpleasant disulfiram/alcohol reaction which is characterized by nausea, a ruddy complexion, palpitation of the heart, low blood pressure, vomiting, and a pulsating headache.

Theoretically, treatment with disulfiram should make an alcoholic abstain from drinking alcohol. However, it has been found, in actual practice, that treatment with disulfiram frequently fails because the patient stops taking disulfiram and then resumes his drinking. The reason is that disulfiram can only be administered orally in the form of tablets or as a mixture and therefore requires daily administration.

In view hereof, there is need of a different form of administration by which disulfiram can be taken systematically in the form of a depot drug from which the substance is slowly released.

For many years, the so-called "implantation technique" has been tried, by which disulfiram tablets are inserted under the skin by operative surgery. However, experience has shown that this treatment has no effect because disulfiram is released so slowly that the patient experiences no disulfiram/alcohol reaction when consuming alcohol.

In course of time, several injection drugs containing disulfiram have been proposed. USSR patent specification 390,206 proposes a solution of disulfiram in benzyl benzoate and vegetable oil. M. Phillips, in U.S. Pat. specification No. 4,678,809, has proposed the intramuscular injection of disulfiram as an aqueous suspension, or operated into a matrix of poly(lactic acid-co-glycolic acid). The specification of EP 0,169,618 proposes injecting disulfiram in a uniform microcrystalline form suitable for absorption by the reticulo-endothelial system.

However, none of these forms of administration has found to be useful in actual practice. The reason is that disulfiram mainly acts by an irreversible blocking of a liver enzyme, acetaldehyde dehydrogenase. Alcohol is metabolised mainly in the liver. The first step of this metabolism is an enzymatic oxidation to acetaldehyde which is then oxidised by another enzyme system called acetaldehyde dehydrogenase which is the enzyme irreversably blocked by disulfiram.

When a patient undergoing disulfiram treatment consumes alcohol, an accumulation of acetaldehyde occurs which leads to the above-mentioned toxic reactions in the disulfiram/alcohol reaction.

If disulfiram is taken perorally, it will, like other drugs, after intestinal absorption be immediately carried to the liver via the portal vein system.

It is known that disulfiram, besides being very sparingly soluble in water, is metabolised very quickly in blood at a $t^1/2$ of but 4 min. It may therefore be assumed that disulfiram can be administered only perorally because this is the only way in which it can affect the liver enzyme acetaldehyde dehydrogenase to a sufficient degree. If disulfiram is given parenterally, for example in the form of an injected local depot in a muscle, it will never reach the liver in such quantities that a therapeutical effect is obtained.

This shows that there is a definite need of novel compounds which have the therapeutical effect of disulfiram, but whose physiochemical properties are better suited for parenteral administration so that suitable depot formulations can be prepared from these compounds.

Substituted S-alkyl esters of thiocarbamic acid have been known for many years. For example, H. Tilles (JACS 81, page 714, 1959) has prepared 256 thiocarbamic acid esters with different substituents on the N atom for the purpose of developing novel herbicides.

GB patent specification 868,111 discloses 140 thiocarbamic acid esters with herbicidal activity. Many of the thiocarbamic acid esters here described have since then found widespread use as vermicidal agents. For environmental reasons, these thiocarbamic acid esters have been thoroughly investigated in respect of toxicity, but there are no reports on effects showing that substances of this type are capable of blocking the enzyme acetaldehyde dehydrogenase, thereby to produce a disulfiram/alcohol reaction.

The invention relates to substituted carbamic acid esters of the general formula I

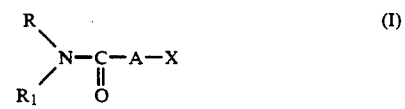

wherein X is —CH$_3$ or —CH$_2$CH$_3$, R and R$_1$ which may be the same or different, are hydrogen, C$_{1-5}$ alkyl or a group of the formula

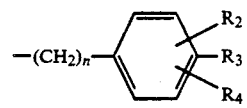

wherein n is 0, 1 or 2, and R$_2$, R$_3$ and R$_4$ are H, OH, OCH$_3$, CH$_3$, NO$_2$ or halogen, and wherein R and R$_1$ together with the nitrogen atom can form a saturated ring system having 4–6 atoms selected among C, N, O or S, and wherein A is sulphur or oxygen.

In a special embodiment, the invention relates to substituted thiocarbamic acid esters of the general formula II

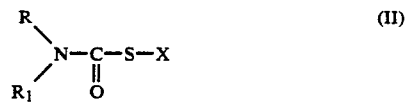

wherein X is —CH$_3$ or —CH$_2$CH$_3$, R and R$_1$ which may be the same or different, are hydrogen, C$_{1-5}$ alkyl or a group of the formula

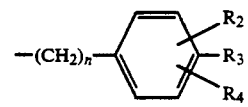

wherein n is 0, 1 or 2, and R$_2$, R$_3$ and R$_4$ are H, OH, OCH$_3$ CH$_3$ NO$_2$ or halogen, and wherein R and R$_1$ together with the nitrogen atom can form a saturated ring system having 4-6 atoms selected among C, N or S.

It has now surprisingly been found that carbamic acid esters of the above-mentioned type are highly potent inhibitors of acetaldehyde dehydrogenase, as is evidenced by the following tests.

METHOD FOR INHIBITING ALDEHYDE DEHYDROGENASE

Fractionation of rat liver homogenates was performed according to Tottmar et al, Biochem. J. 1973:135:577. The aldehyde dehydrogenase activity in the homogenate after incubation for 1 h with different thiocarbamic acid esters (see Table 1) was measured spectrophotometrically in 50 μl aliquots by following the reduction of NAD to NADH at 340 nm at 37° C. in the presence of the substrate acetaldehyde 0.025 μmol/liter, as described by Tottmar and Marcher (Acta Pharmacol. et Toxicol. 1976:38:366). These tests gave the results indicated in Table 1.

Method of assessing the "Antabuse ®-alcohol" reaction on rats by tonometry

These measurements were performed on a selected compound. The substance employed is diethyl thiocarbamic acid-S-methyl ester (referred to as DTSM hereinafter).

Male rats having a body weight of 300-400 g were anaesthetised with urethane 1.25 g/kg i.p. On a group of 4 rats, a catheter filled with heparin-salt water was inserted by operative surgery in one carotid artery, and the blood pressure was recorded before and after intraperitoneal injection of ethanol (1 g/kg, 10 ml/kg of 10% v/v ethanol in water). Two other groups of 3 rats each were treated intraperitoneally with DTSM for 1 and 2 hours, respectively, whereupon ethanol (1 g/kg, 10 ml/kg of 10% v/v ethanol in water) was injected intraperitoneally. The blood pressure was measured before the injection of ethanol and for 30 min. after injection, after which time the blood pressure has usually stabilized itself (Hellström and Tottmar: Pharmacology Biochemistry and Behaviour 1982:17:1103).

The results are shown in Table 2.

TABLE 1

In vitro inhibition of aldehyde dehydrogenase of low $K_m$ with different thiocarbamic acid esters of the general formula

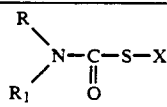

| X | R | $R_1$ | Residual activity of aldehyde dehydrogenase (Low $K_m$ in % of ref. value) |
|---|---|---|---|
| $CH_3$ | $CH_3$ | $CH_3$ | 16 |
| $CH_3$ | $CH_2CH_3$ | $CH_2CH_3$ | 73 |
| $CH_2CH_3$ | $CH_2CH_3$ | $CH_2CH_3$ | 8 |
| $CH_3$ | $CH_2CH_2CH_3$ | $CH_2CH_2CH_3$ | 11 |
| $CH_3$ | —CH$_2$—CH$_2$—CH$_2$—CH$_2$— (ring) | | 9 |
| $CH_3$ | CH$_2$(CH$_2$CH$_2$—)$_2$ (ring) | | 16 |
| $CH_3$ | $CH_2$—$CH_2$—C$_6$H$_4$—OH | H | 10 |
| $CH_3$ | $CH_2$—$CH_2$—C$_6$H$_5$ | H | 0 |
| $CH_3$ | C$_6$H$_5$— | H | 8 |
| Water (Ref.) | | | 100 |
| Diethyl carbamic acid-methyl ester | | | 87* |
| 1-piperidine carbamic acid-methyl ester | | | 76* |

*Measured on bovine liver

The values are X±SD of double determinations, on the one hand in homogenates from 4 rats and, on the other hand, in bovine liver (last two values in Table 1).

The concentration=2760 μmol/liter for all compounds, except the last two compounds for which the concentration was 3.0 mmol/liter.

TABLE 2

| Pretreatment and time | Diastolic blood pressure of rats 30 min. after ethanol injection | |
|---|---|---|
| | % of own ref. value* $X \pm SD (N) \rightarrow$ | p value (Student's test) |
| Salt water 1 hour | 92.5 ± 5.2 (4) | — |
| DTSM 30 mg/kg i.p. 1 hour | 77.1 ± 3.6 (3) | <0.01 |
| DTSM 30 mg/kg i.p. 2 hours | 57.6 ± 28 (3) | <0.05 |

*measured before ethanol injection

Substituted thiocarbamic acid esters according to the invention can be prepared in per se known manner. The techniques stated in "Houben-Weyl, Methoden der Organische Chemie", Vol. 9, pp 834-37, are eminently suitable for preparing the compounds according to the present invention.

The carbamic acid esters of formula I wherein A is oxygen, can also be prepared in per se known manner, for example in accordance with R.O. House in "Modern synthetic reactions", W.A. Benjamin, INC, California, 1972, pp 602-604. By this technique, for example 1-piperidine carboxymethyl ester can be prepared from piperidine and chloroformylmethyl ester.

The substituted carbamic acid esters here referred to are solid or liquid substances that can be taken like a conventional drug in the form of capsules, tablets or a mixture. However, they are especially suitable for parenteral administration, in particular as constituents of a depot preparation of prolonged release.

The compounds according to the invention can thus be taken in a vegetable oil, in a fat emulsion, or as micelles.

The following Examples illustrate the possibilities of using the compounds, but must not be regarded as restrictive Examples.

EXAMPLE 1

8 g diethyl thiocarbamic acid-S-methyl ester is dissolved in 90 g peanut oil. 2 g benzyl alcohol is added as a preservative. The mixture is poured into 5 ml glass ampoules which are then sterilized at 120° C. for 20 min.

EXAMPLE 2

16 g dimethyl thiocarbamic acid-S-methyl ester is dissolved in 80 g soybean oil. 5 g egg lecithin, 10 g glycerol and 100 ml sterile water are added, and from this mixture a stable emulsion is prepared which is heat-treated and then poured aseptically into 5 ml stoppered tubes.

EXAMPLE 3

30 g egg lecithin, 20 g sodium glycocholate and 30 g N-(para-hydroxyphenetyl)-carbamic acid-S-methyl ester are dissolved in 100 ml ethanol. The solution is evaporated to dryness in a rotary evaporator. Adding an aqueous phosphate buffer gives a limpid micelle solution which is poured aseptically into ampoules.

EXAMPLE 4

8 g diethyl thiocarbamic acid-S-ethyl ester is dissolved in 80 g glycerol monooleate to which 12 g egg lecithin is added. The mixture is sterilized by heat treatment and poured into 5 ml ampoules.

We claim:

1. A method of treating addiction to alcohol in a patient comprising administering to said patient an effective amount of a compound of the general formula:

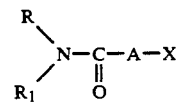

wherein:
 (a) X is $CH_3$ or $CH_2CH_3$;
 (b) A is S or O;
 (c) R and $R_1$, which may be the same or different:
  (i) are selected from the group consisting of hydrogen, $C_{1-5}$ alkyl, and a group of the formula:

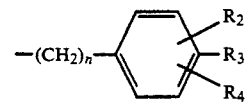

wherein:
   (A) n is 0, 1, or 2; and
   (B) $R_2$, $R_3$, and $R_4$ are H, OH, $OCH_3$, $CH_3$, $NO_2$, or halogen; or
  (ii) form a saturated ring system, with the amide nitrogen atom, having 4-6 atoms selected from the group consisting of C, N, O, and S.

2. The method according to claim 1 wherein the compound is administered parenterally.

3. The method according to claim 2 wherein the compound is administered in a depot preparation for prolonged release.

4. The method according to claim 1 wherein the compound is administered in a preparation of a vegetable oil, a fat emulsion, or micelles.

5. The method according to claim 1 wherein A is S.

* * * * *